United States Patent [19]

Jackman et al.

[11] Patent Number: 4,578,463
[45] Date of Patent: Mar. 25, 1986

[54] PRODUCTION OF S-SUBSTITUTED ISOTHIOUREAS

[75] Inventors: Dennis E. Jackman, Prarie Village; Dietmar B. Westphal, Lenexa, both of Kans.

[73] Assignee: Mobay Chemical Corporation, Pittsburgh, Pa.

[21] Appl. No.: 632,136

[22] Filed: Jul. 18, 1984

[51] Int. Cl.$^4$ .................. C07D 253/00; C07D 239/02; C07C 119/18
[52] U.S. Cl. ........................................ 544/182; 558/5; 544/315; 544/309
[58] Field of Search ..................... 260/453.4; 544/182, 544/315, 309

[56] References Cited

U.S. PATENT DOCUMENTS 4,055,572 10/1977 Dawes et al. ................. 260/453.4

OTHER PUBLICATIONS

Morrison & Boyd, 3rd Edition, Organic Chemistry, p. 360.

Primary Examiner—Henry R. Jiles
Assistant Examiner—Robert C. Whittenbaugh
Attorney, Agent, or Firm—Sprung Horn Kramer & Woods

[57] ABSTRACT

A process for the production of an S-substituted isothiourea including the functional group

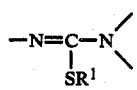

in which
R$^1$ is an alkyl, alkenyl, aryl or aralkyl radical, comprising reacting a thiourea including the functional group

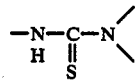

with an alpha-activated etherifying agent of the formula

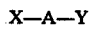

in which
  X is a halogen atom,
  A is a direct bond or CH$_2$, and
  Y is an electron withdrawing group, thereby to produce the ether

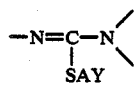

and in a second step reacting the ether with a compound of the formula R$^1$SH. The process is particularly applicable to the production of the known herbicide

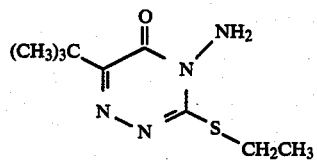

from the corresponding thiourea where in the first step chloroacetic acid is used to form the S-carboxymethyl isothiourea which is then interchanged with ethyl mercaptan. Higher overall yields and/or economies are thereby achieved.

12 Claims, No Drawings

PRODUCTION OF S-SUBSTITUTED ISOTHIOUREAS

The present invention relates to a process for converting a thiol to a thio ether, particularly wherein the starting material is a thiourea.

U.S. Pat. No. 3,671,523 discloses the extremely effective selective herbicide of the formula

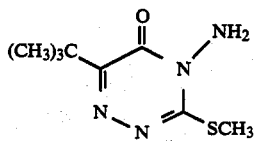

The compound is produced by methylating the corresponding compound having an —SH radical in the 3-position with a methylating agent such as methyl bromide or methyl iodide, methyl chloride producing much lower yields. While the process works well (with some methylation of the N-2 atom), methyl bromide and iodide are relatively expensive.

U.S. application Ser. No. 303,658, filed Sept. 18, 1981, now pending, discloses a similar process for making the compound

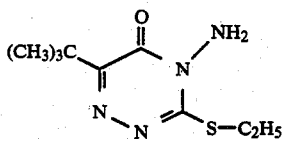

which is also selectively herbicidal, employing ethyl bromide and iodide which are even more expensive than methyl bromide and iodide.

The art includes disclosures of several other triazinones which carry an S-alkyl substituent in 3-position and other substituents in 4-and 6-positions but, for practical economic considerations, they are produced from expensive alkylating agents reacting with the corresponding 3-thiols.

It is accordingly an object of the present invention to produce S-substituted isothioureas in a simple inexpensive manner.

It is a further object of the invention to produce thioethers from the corresponding mercaptans in an inexpensive manner.

These and other objects and advantages of the invention are realized in accordance with the present invention pursuant to which there is provided a process for going from the thiourea

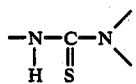

to the corresponding S-substituted isothiourea having the functional group

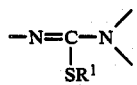

by reacting the thiourea with an alpha-activated alkyl halide to produce an isothiourea and then exchanging the ether radical by reaction with mercaptans of the general formula $R^1SH$.

Illustratively,

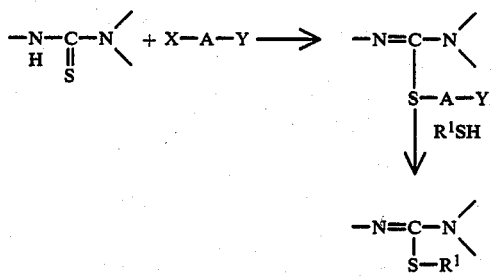

In the general formula X is halide, especially chloride or bromide, A is a direct bond or, preferably, $CH_2$ and Y is an activating (electron withdrawing) group such as carboxyl, acyl, nitro, cyano, sulfonyl, sulfinyl, trifluoromethyl, or other electronically similar radical, and advantageously $R^1$ is an alkyl, alkenyl, aryl or aralkyl radical, the aliphatic radicals preferably containing up to 12 and especially up to 4 carbon atoms.

The process is particularly applicable to starting materials including a heterocyclic ring and especially to those wherein the thiourea structure is part of the ring, e.g. suitably substituted pyrimidines (uracils), 1,3,5-triazines, and the like. Most preferred, however, are starting materials of the formula

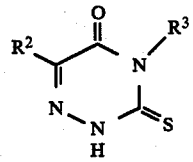

in which $R^2$ is an alkyl, alkenyl, aryl or aralkyl radical, and $R^3$ is an alkyl, amino or alkylideneimino radical, particularly those wherein $R^2$ is an alkyl or alkenyl radical containing up to 12 carbon atoms, or a phenyl radical, and $R^3$ is an $NH_2$ radical, or an alkyl, alkenyl, aryl, aralkyl, alkylamino, alkenylamino or arylamino radical containing up to 12 carbon atoms, and especially those wherein $R^2$ is branched alkyl containing up to 6 carbon atoms, e.g. tert-butyl, fluoro- or chloro-tert.-butyl and branched pentyl containing a quaternary carbon atom, and $R^3$ is $NH_2$ or alkyl, alkylamino or dialkylamino containing up to 4 carbon atoms, especially $NH_2$ or methyl.

Advantageously both steps of the reaction are effected in a solvent and in the presence of a catalyst with removal of by-product HSAY by extraction.

The reaction temperature can range from room temperature or even lower up to the boil, depending upon the solvent employed, but preferably is from about 30° to 100° C.

Suitable solvents include inert organic solvents such as toluene, halogenated hydrocarbons, or the like, but the use of water is preferred when the reagent or end product is water-soluble, e.g. chloroacetic in the presence of alkali.

Thus, while the reactants can be employed in stoichiometric quantities, large excesses of either of the reactants can be employed, preferably of the less expensive reactant, to drive the reactions to completion.

The reactions employing a thiourea and chloroacetic acid can be illustrated as follows:

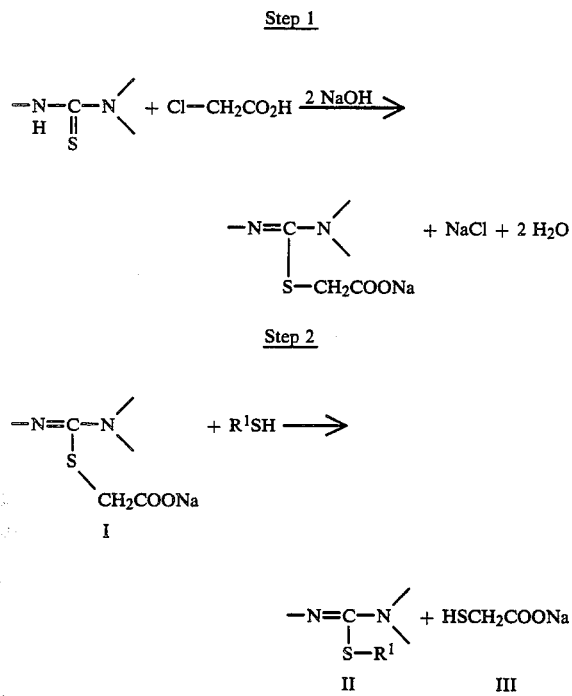

The chloroacetic acid is converted to the Na salt and the thiol to the Na salt in Step 1. In Step 2, I (water soluble) reacts with $R^1SH$ (water insoluble) to form II (water insoluble-soluble in excess $R^1SH$) and III (water soluble). The reaction is reversible but goes forward because II and III have different solubilities. III is removed by extraction into water.

The reaction utilizes 2 equivalents of NaOH and preferably more (~0.3 mole) in Step 2 to maintain pH 9. This is not necessary to make the reaction work, but is advantageous for yield and purity. In this case the by-product III is really a mixture of $HSCH_2COONa$ and $NaSCH_2COONa$. This higher pH also helps the reaction because some $R^1SH$ is converted to $R^1SNa$ which is probably what attacks I to form the products.

A variety of alpha-activated halides can be employed to form the isothiourea in the first step, e.g. cyanogen chloride, bromonitromethane, chlorodimethylsulfone, chloroacetone, 4-nitrobenzyl chloride, 2,4-dinitrobenzyl chloride and the like.

However, bromoacetic acid and especially chloroacetic acid are highly preferred. This is because in etherification they have proven especially selective compared to other agents which undesirably etherify the urea nitrogen atom to varying degrees. For example, in the first stage etherification the percentages of undesired N-alkylation (balance to 100% representing desired S-alkylation) with various alkylating agents can be seen in the following table:

| % N—ALKYLATION WITH DIFFERENT ALKYLATING AGENTS | | |
|---|---|---|
| Br—CH$_2$—CH$_3$ | Br—CH$_2$—H | Br—CH$_2$—CO$_2$H |
| 16 | 6 | 0 |
| Cl—CH$_2$CH$_3$ | Cl—CH$_2$H | Cl—CH$_2$CO$_2$H |
| 80–90 | 30–40 | 0 |

The reaction of the activated chloride with the thiourea can be effected in aqueous solution if desired, possibly adjusting the pH to establish solubility, e.g. chloroacetic acid in alkaline solution. The reaction can be speeded up by the presence of a small amount of sodium bromide which apparently functions catalytically and which can be recovered at any appropriate stage, e.g. after etherification or after ether interchange.

While not limited thereto, the invention is especially useful in producing the following compounds in addition to that exemplified hereinbelow and those shown in Application Ser. No. 632,132, filed July 18, 1984 simultaneously herewith, the disclosure of which is incorporated herein by reference:

4-amino-3-methylthio-6-tert.-butyl-1,2,4-triazin-5-one
4-amino-3-ethylthio-6-tert.-butyl-1,2,4-triazin-5-one
1-amino-6-ethylthio-3-(2,2-dimethylpropyl)-1,3,5-triazine-2,4(1H,3H)-dione
4-amino-6-chloro-tert.-butyl-3-propargylthio-1,2,4-triazin-5-one
4-amino-6-fluoro-tert.-butyl-3-allylthio-1,2,4-triazin-5-one
4-amino-6-fluoro-tert.-butyl-3-methylthio-1,2,4-triazin-5-one
4-amino-6-(1,1-bis-fluoromethyl-ethyl)-3-buten-2-ylthio-1,2,4-triazin-5-one
4-amino-6-ethoxy-tert.-butyl-3-propargylthio-1,2,4-triazin-5-one
6-(2,3-dimethyl-but-2-yl)-4-methyl-3-methylthio-1,2,4-triazin-5-one
4-amino-6-cyclobutyl-3-methylthio-1,2,4-triazin-5-one
6-cyclobutyl-4-isopropylideneamino-3-methylthio-1,2,4-triazin-5-one The invention will be further described with reference to the following illustrative example wherein all parts are by weight unless otherwise expressed:

EXAMPLE

A mixture of 200 g (1 mole) of 4-amino-6-t-butyl-3-mercapto-1,2,4-triazin-5-one, 200 ml of water, 20.6 g (0.2 mole) of sodium bromide, and 108 g (1.14 mole) of chloroacetic acid was stirred and treated with 25% NaOH until the pH reached 9.5. The solution was then stirred and heated at 50° C. while maintaining a pH of 9.5 until the reaction was complete (usually 3–5 hrs). After cooling to below 30° C., ethyl mercaptan (372 g, 6 mole) was added and the mixture stirred and refluxed at pH 9–9.5 until the intermediate 4-amino-6-t-butyl-3-carboxymethyl-1,2,4-triazin-5-one was entirely reacted (tlc), the usual time being 3–5 hours. The upper organic layer was then removed, mixed with 200–300 ml water and the excess ethylmercaptan recovered by distillation. The aqueous suspension of 4-amino-6-t-butyl-3-ethylthio-1,2,4-triazin-5-one was filtered to give the product in about 95% yield with purity of 98–99%.

It will be understood that the specification and examples are illustrative but not limitative of the present invention and that other embodiments within the spirit and scope of the invention will suggest themselves to those skilled in the art.

We claim:

1. In the production of an S-substituted isothiourea including the functional group

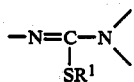

in which $R^1$ is an alkyl, alkenyl, aryl or aralkyl radical, wherein a thiourea including the functional group

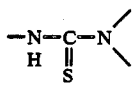

is reacted with an etherifying agent to replace H by $R^1$, the improvement which comprises effecting the reaction in two steps, in the first step reacting the thiourea starting material with an alpha-activated etherifying agent of the formula X—A—Y in which X is halogen A is a direct bond or $CH_2$, and Y is an electron withdrawing group thereby to produce the ether

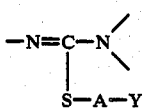

and in the second step reacting the ether with a compound of the formula $R^1SH$.

2. The process according to claim 1, wherein the etherifying agent in the first step is an alpha-activated alkyl halide.

3. The process according to claim 1, wherein the starting compound is of the formula

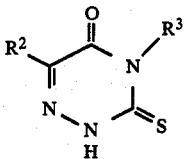

in which $R^2$ is an alkyl, alkenyl, aryl or aralkyl radical and $R^3$ is an alkyl, amino or alkylideneimino radical.

4. The process according to claim 3, in which $R^2$ is an alkyl radical of up to 6 carbon atoms or phenyl, optionally substituted by halogen and/or $C_{1-4}$-alkoxy, $R^3$ is an amino, alkyl, alkylamino, dialkylamino or alkylideneimino radical each containing up to 6 carbon atoms.

5. The process according to claim 4, in which

XAY is chloroacetic acid or bromoacetic acid, $R^2$ is branched alkyl containing up to 6 carbon atoms or phenyl each optionally including a halogen atom, and $R^3$ is methyl or amino.

6. The process according to claim 5, in which $R^1$ is $C_2H_5$, $R^2$ is $C(CH_3)_3$, and $R^3$ is $NH_2$.

7. The process according to claim 1, wherein the first step is effected in water under alkaline conditions.

8. The process according to claim 7, wherein sodium bromide is present as a catalyst.

9. A process according to claim 1, wherein during or after the second step of the reaction the by-product of the formula HSAY is removed from the principal product by extraction into water.

10. A process according to claim 1, wherein the second step is effected in the presence of a catalyst comprising an alkali metal or ammonium hydroxide, an amine, an alkaline imide, an alkal metal alkaline salt or a quaternary ammonium hydroxide.

11. The process according to claim 5, in which $R^1$ is $CH_3$, $R^2$ is $C(CH_3)_3$, and $R^3$ is $NH_2$.

12. The process according to claim 5, in which $R^1$ is alkyl with up to 4 carbon atoms.

* * * * *